United States Patent [19]

Hirschfeld

[11] 4,166,105

[45] Aug. 28, 1979

[54] DYE TAGGED REAGENT

[75] Inventor: Tomas Hirschfeld, Framingham, Mass.

[73] Assignee: Block Engineering, Inc., Cambridge, Mass.

[21] Appl. No.: 535,095

[22] Filed: Dec. 20, 1974

Related U.S. Application Data

[63] Continuation-in-part of Ser. No. 383,892, Jul. 30, 1973, abandoned.

[51] Int. Cl.² .................. A61K 29/00; G01N 31/00; G01N 31/22; G01N 33/16
[52] U.S. Cl. .......................................... 424/8; 424/3; 424/7; 424/2; 424/12; 23/230 B; 260/6; 260/112 R
[58] Field of Search ................ 424/3, 7, 8, 12; 260/6, 260/112 R; 250/461 B, 459; 23/230 B

[56] References Cited

U.S. PATENT DOCUMENTS

| | | | |
|---|---|---|---|
| 3,553,310 | 1/1971 | Csizmas et al. | 424/8 |
| 3,636,023 | 1/1972 | Murray et al. | 8/100 |
| 3,641,235 | 2/1972 | Weiss | 424/8 |
| 3,789,116 | 1/1974 | Kay | 424/8 |
| 3,796,634 | 3/1974 | Haynes et al. | 195/63 |
| 3,816,492 | 1/1974 | Stretanski | 8/100 |
| 3,853,987 | 12/1974 | Dreyer | 424/8 |
| 3,970,597 | 7/1976 | Sokolovsky | 260/6 |
| 4,016,149 | 4/1977 | Travis et al. | 260/122 |

OTHER PUBLICATIONS

Unger Waron CA vol. 79, 1973, No. 103454m.
Nature, vol. 249, No. 5452, pp. 81–83, May 3, 1974.

*Primary Examiner*—Donald B. Moyer
*Attorney, Agent, or Firm*—Schiller & Pandiscio

[57] ABSTRACT

Reagents for the detection of specific reactants, such as antigens in biological fluids, comprising a polymer coupled to an antibody, the polymer having a plurality of dye molecules coupled thereto. The reagent is prepared by covalently linking an end functional group of polymers such as polyethylene amine to an antibody, typically through an aldehyde linkage, the polymer molecule having had a plurality of dye molecules, coupled to the polymer through side reactive sites.

24 Claims, No Drawings

DYE TAGGED REAGENT

This application is a continuation-in-part of copending application Ser. No. 383,892, filed July 30, 1973 now abandoned.

The present invention relates to analytical systems using reagents molecularly tagged with radiant energy emitters, and more particularly to reagents useful in the detection of antigenic-type reactants and a method of using that reagent for the stated purpose.

The technique of detecting and classifying reactants in a highly specific reaction, such as the antigen in an antigen-antibody reaction, by tagging one of the reactants (such as the antibodies) with a radiant energy emitter, is known in the art. This method depends upon the ability of the observer to distinguish between the product or complex of the antigen with tagged antibody, and the uncomplexed tagged antibodies. For this purpose various radiant energy detection instruments may be utilized depending on the nature of the energy emitter.

Current methods for detecting antigens with tagged antibodies suffer from a number of serious disadvantages, particularly the lack of sufficient signal level associated with small quantities of antigen. Many cases of serious disease having an antigenic etiology thus remain unnoticed, resulting in unnecessary suffering, and in some cases, death.

In cases where the radiant energy emitter is radioactive, the reagent containing the tagged antibody produces a potential hazard to the manufacturers of the reagent and to the clinical laboratory people carrying out an assay with the reagent. Additionally, transportation of such radioactive reagents is becoming subject to increasingly onerous restrictions. The photoemission from each radioactive atom is, or course, very meager. Lastly, if the half-life of the radioactive emission is short, as is often the case, the signal level of the radioactive emission may diminish so rapidly that the shelf life of the reagent is severly limited.

In many cases, antibody tagging is done with a coupled fluorescent dye molecule, e.g. either a dye which is capable of fluorescent emission with a reasonably high quantum efficiency when directly excited by radiation in its absorption band, or a fluorochrome dye which fluoresces with a substantially greater quantum efficiency when bound to the antibody than when present as a free dye molecule. Typically, dyes such as fluorescein, rhodamine, pyronine, eosin, acridine, acriflavine, safranine, methylene blue and a host of other dyes have been used in this prior art technique together with appropriate photometric detection devices. The signal level of fluorescent dyes bound to an antibody-antigen complex in the prior art was generally too low for individual particle detection to be made. Prior art efforts to improve this sensitivity by increasing the dye loading (the number of bound dye molecules coupled to each antibody), resulted in a reduction of the specificity and sensitivity of the antibody-antigen reaction, and a number of reasons can be postulated for this reduction:

(1) when enough dye molecules become coupled to the antibody, some of them will be close enough to the antigen-specific bonding site to produce partial steric shielding;

(2) changes in the overall hydrophilicity and net charge of the resulting dye-antibody molecule will alter its reactivity and solubility;

(3) steric and hydrophilicity stresses on the dye-antibody molecule, as well as possible changes in its vibrational behavior, may distort the protein's tertiary structure and consequently its specificity;

(4) chemical interactions at the dye-antibody bond site may cause alteration of the atomic bonding for some distance away from the link's location, possibly involving the specific binding site.

The present invention overcomes these problems of the prior art by a novel, advantageous system which increases the number of fluorescent dye molecules bonded to the antibody molecule consistent with maintaining the antibody-antigen specificity essentially unimpaired. To this end, the present invention is embodied in a reagent comprising an antibody molecule to which has been covalently attached a large number of fluorescent dye molecules through a polymeric backbone having reactive, functional groups along the length of its chain. Thus, the attachment, at a single site on an antibody, of a polymeric chain having a multiplicity of fluorescent moieties, increases very substantially the magnitude of fluorescent emission (under appropriate excitation) from the combined molecule while minimally affecting the specificity of the reactivity of the antibody with its antigen. It is thus a principal object of the invention to increase dye loading in specific antibody immunofluroescence without substantially impairing specificity.

It is a further object of the invention to improve the sensitivity of antibody immunofluorescence techniques by at least two orders of magnitude over the prior art.

The terms "first reactant" and "second reactant" (hereinafter termed "analyte") as used herein are intended to be construed in a broad physical sense. The first reactant can be an antibody or any chain molecule having two or more reactive sites (or functional groups) so sterically separated from one another and disposed that one of the sites can be bonded to the carrier polymer without impairing substantially the specific reactivity of the other of the sites with the analyte body. Typically, the first reactant can be biological, i.e. blood serum proteins, the formation of which is biologically mediated in response to the presence of an analyte in the form of an antigen, or nonbiological, e.g. ligands including organic sequestering and chelating agents, and the like. Analytes are substances which react, preferably with high specificity, with a particular first reactant, each analyte particle or body having a plurality of reactive sites so that it couples with a plurality of molecules of first reactant. Analytes thus are deemed to include biological antigens which typically are high molecular weight (e.g. $>10,000$) complex organic molecules, such as enzymes, toxins, proteins, possibly polysaccharides and lipoproteins, whole microorganisims, such as bacteria, viruses, protozoa and the like, both live and dead, and haptenes or substances that can react with an antibody but cannot of themselves engender biological formation of an antibody. Such biological analytes or antigens of course are specifically reactive with corresponding biological antibodies by definition. Non-biological analytes which are reactive with corresponding ligands can be as simple as a metallic ion, molecular cluster or the like.

The carrier or backbone molecule polymer chosen has reactive sites dispersed along the length of the chain, with a chemically different reactive site at the end of the chain. This carrier polymer molecule should either be rigid or tend to fold to a globular configuration in water, so as to prevent steric impediments arising out of its unfolding or twisting around. Its net ionic charge (when aggregated with dye molecules attached to its side linkages) per unit volume should be essentially the same as that of the first reactant when the latter is an antibody, at the working pH. The reactive sites dispersed along the length of the chain of the carrier polymer molecule should have a low affinity for the first reactant and should not act as fluorescence quenchers. Preferably the carrier polymer molecule has hydrophilicity similar to the first reactant. The backbone of the polymer molecule should include covalent bonding sites separated by a sufficient distance to avoid disruption of the useful spectral properties of the dye moieties caused by perturbation effects of one dye molecule interacting through space with another dye molecule.

The term "specific" as used herein is intended to describe a reaction in which the reactants will react substantially only with each other and to much lesser or negligible degree with other reactants, such reaction being particularly exemplified by an antibody-antigen reaction.

Polymer backbone molecules suitable for the practice of this invention are polyethylenimines, suitably of molecular weight in the range of 1200–60,000,, polypeptides such as polylysines, polyamides such as nylon-6, low molecular weight [100–10,000] polymeric carboxylic acids, and other polymeric materials containing repeating reactive functional groups along the length of their chain.

The polymeric backbone substance is tagged with dyes by being allowed to react with fluorescent dye molecules, each of which has a reactive group so that it can react covalently with the repeating functional groups of the polymeric material. Prior to reaction with the fluorescent dye molecule, the reactive end groups of the polymer molecule are temporarily blocked or chemically protected as by reaction with a carbonyl compound. Suitable carbonyl compounds for this purpose are exemplified by benzaldehyde, glutaraldehyde, etc.

Fluorescent dyes suitable for use in the present invention when functionalized include, but are not limited to, the following:

| Acid Violet 4BL | C.I. No. 42575 |
| --- | --- |
| Acridine Brilliant Orange | C.I. No. 46005 |
| Acridine Orange | C.I. No. 46005 |
| Acridine Yellow | C.I. No. 56025 |
| Acriflavine | C.I. No. 46000 |
| Auramine 0 | C.I. No. 41000 |
| Aurophosphine G | C.I. No. 46035 |
| Benzo Flavine | C.I. No. 46035 |
| Berberine Sulfate | C.I. No. 75160 |
| Brilliant Phosphine | C.I. No. 46035 |
| Brilliant Sulfo Flavine | C.I. No. 56205 |
| Chrysoidine | C.I. No. 11270 |
| Coerulein S | C.I. No. 45510 |
| Coriphosphine 0 | C.I. No. 46020 |
| Coriphosphine Fuchsin | C.I. No. 42755 |
| Euchrysine 2G | C.I. No. 46040 |
| Euchrysine 3 RX | C.I. No. 46005 |
| Flavo Phosphine R. | C.I. No. 46035 |
| Fluorescein | C.I. No. 45350 |
| Geranine G | C.I. No. 14930 |
| Methylene Blue | C.I. No. 52015 |
| Morin | C.I. No. 75660 |
| Neutral Red | C.I. No. 50040 |
| Orange G | C.I. No. 16230 |
| Phosphine 3R | C.I. No. 46045 |
| Primuline | C.I. No. 49000 |
| Pyronin GS (Pyronin extra) | C.I. No. 45005 |
| Rhoduline Orange | C.I. No. 46005 |

-continued

| Rhoduline Violet | C.I. No. 29100 |
| --- | --- |
| Rosole Red B | C.I. No. 43800 |
| Safranin | C.I. No. 50210 |
| Scarlet R | C.I. No. 26105 |
| Sulpho Rhodamine B | C.I. No. 45100 |
| Tartrazine 0 | C.I. No. 19140 |
| Thiazine Red R | C.I. No. 14780 |
| Thiazol Yellow | C.I. No. 19540 |
| Thioflavine S. | C.I. No. 49010 |
| Thionin | C.I. No. 52000 |

After the dye molecules are coupled through the reactive side groups of the polymer, two slightly different procedures are used depending upon whether a monoaldehyde or a polyaldehyde has been used to block the reactive end group of the polymer. If a monoaldehyde such as benzaldehyde is used as a protective agent, following dye coupling to the polymer the benzaldehyde moiety is removed, as by hydrolysis, to reactivate the end site. The latter is then functionalized in preparation for covalent attachment to the antibody molecule.

Alternatively, if a polyaldehyde such as glutaraldehyde (propanedial) is used (preferably in a large excess) as a protective agent for the reactive end site of the polymer, the protective glutaraldehyde moiety need not be removed but can serve as a linking agent for covalent attachment of the polymer to the antibody or other first reactant.

The dye-polymer complex is then coupled to the first reactant, such as an antibody, to provide a dye-/polymer/antibody complex. The reagent is buffered if necessary so that the dye/polymer/antibody molecules are preferably electrically neutral, such neutrality minimizing impairment of the specific reactivity between the first reactant and the analyte, particularly an antibody-antigen reaction. One can change the pH of the reagent with known buffers in the range between pH values at which, for antibody-antigen type reactions, protein denaturing may occur, i.e. between pH 4 and 10 approximately. Thus, any excess charge on the reagent molecules should be in weakly ionized groups, such as carboxy or amino groups, the pK of which is between about 4 and 10.

The dye/polymer/antibody complex or reagent will, when mixed with a solution containing antigen specific to the antibody in the complex, couple to the antigen. Because the analyte body with which the reagent of the present invention is reactive, may possess several attachment sites, each analyte body then may have coupled to it two or more of the reagent molecules. Observation of a flow stream of minute cross-section (or some other known technique for segregating molecules from one another) irradiated with light in the absorption band of the dye of the complex will detect fluorescence from each reagent molecule in the flow stream sequentially passing the area of irradiation. By threshholding the measurement of the amplitude of each fluorescent pulse detected, one can readily discriminate between each point source which produced low level signals due to simple unbound reagent molecules and the greater amplitude signals obtained from each plurality of reagent molecules bound to a single analyte body, thereby identifying the presence of the analyte. Obviously, one cannot by this technique discriminate between a group of reagent molecules bound to a single analyte body and a group of cross-linked reagent molecules. For this reason, it is important in preparing the reagent of the invention to guard against cross-linking as with appropriate agents temporarily blocking reactive groups, and preferably, before use, the reagent should be subjected to a separation procedure, such as by silica gel chromatography, to fractionate out substantially all cross-linked reagent molecules. In instances where, following reaction between the reagent and an analyte, unreacted reagent can be physically removed, detection of analyte coupled to single reagent molecules becomes feasible.

Preparation of a typical reagent of the present invention is exemplified by reacting polyethylenimine 200 (molecular weight 20,000) with a stoichiometric excess of glutaraldehyde and fractionating the mixture as with a Sephadex column to eliminate excess glutaraldehyde and polymer that has become cross-linked by the polyaldehyde. The protected polymer is reacted with an excess of functionalized dye such as fluoroscein isothiocyanate and the mixture again fractionated to separate free dye from dyed polymer.

Many dyes in functionalized form, such as fluoroscein isothiocyanate, are commercially available. Typically, the fluoroscein is functionalized by the known technique of first adding an extra, non-chromophoric amino group to the fluoroscein molecule, as by nitrating the fluorescein with $NHO_3$ and reducing the nitrate with nascent hydrogen produced by the addition of zinc and HCl. The isothiocyanate is then formed by adding thiophosgene. Of course, other techniques are known to produce functionalized dye by converting them, for example, to isothiocyanate form or by adding other groups such as sulfonyl chloride, or a 2-bromoethyl side chain.

Antibody, commercially obtainable, is preferably fractionated, as with Sepharose, to separate out immunoglobin-m from gamma globulin. The latter fraction is mixed with the dyed polymer and the reaction terminated, as with ethanolamine or trimethylaminomethane hydrochloride, appropriately buffered. This latter reaction is an amino-aldehyde reaction which arrests further linking between the dyed polymer and other antibodies. The mixture must then be fractionated as with a Sephadex column to separate the antibody/polymer/dye molecules according to the number of polymer molecules coupled to each antibody molecule. Fractions which are antibody only or antibody with two or more polymers are discarded, the former because it is useless being untagged and the latter because it has less specificity and sensitivity than the selected fraction.

Particular antigens detected by the process of this invention are typified by viruses such as Hepatitis B antigen and Echo 12 virus, Hoof and Mouth disease antigen and Swine vesicular disease virus antigen. It will be recognized, however, that the present process is not limited to the detection of those viruses specifically named but is generally applicable to all antigens for which the appropriate antibody is available.

The invention will appear more fully from the examples which follow. These examples are given by way of illustration only and are not to be construed as limited either in spirit or in scope as many modifications both in materials and in methods will be apparent to those skilled in the art.

EXAMPLE I

The formation of a polymer/dye complex is achieved as follows:

To a solution of 2 mg. of polyethylenimine 200 (molecular weight 20,000) in 1 ml. of 0.1 M sodium cacodylate at pH 7.0, 0.1 ml. of 25% aqueous glutaraldehyde is added with vigorous stirring. The resulting reaction mixture is stirred for about 5 minutes and excess glutaraldehyde then removed by passage through a Sephadex G-25 (0.9×15 cm.) (silica gel) column. The column is eluted with 0.1 M, pH 7.2 aqueous sodium cacodylate buffer and to the eluate is added 50 mg. of fluorescein isothiocyanate dissolved in 1.5 ml. of aqueous 0.5 M. pH 9.5 sodium carbonate buffer. The mixture is stirred continuously during the addition and stirring continued for about 16 hours, during which time the mixture is excluded from light. The excess dye is removed by passage through a Sephadex G-25 (silica gel) column (0.9×30.0 cm.) and subsequent elution of the column with 0.1 M, pH 7.0 aqueous sodium cacodylate. 2 ml. fractions are collected.

The resulting polymer/dye complex is analyzed by the Folin-Ciocaulteau protein assay. That assay gives a linear curve with polyethylenimine and thus is suitable for estimation of the amount of polymer present. The Extinction Coefficient of fluorescein isothiocyanate at 495 nm. is $73 \times 10^3$ and drops to 75% of this value on binding. By measuring both polymer and dye present in a given sample of the complex, the degree of dye binding is estimated. This degree of binding depends upon the dye concentration in the initial reaction mixture. Limited fractionation is achieved by gel filtration. The complex prepared by the process of this Example contains approximately 70 dye molecules per molecule of polyethylenimine.

EXAMPLE II

Thee procedure of Example I is followed however altering the molar ratio of dye to polyethylenimine progressively resulting in polymer/dye complexes containing approximately 65 and 80 molecules, respectively, of dye per molecule of polyethylenimine 200.

EXAMPLE III

The procedure of Example I is followed, employing however 0.1 ml of a solution of 25% benzaldehyde is dioxane in place of the glutaraldehyde, to produce a polymer/dye complex similar to that of Example I except that the reactive end sites of each polyethylenimine molecule is coupled to a benzaldehyde moiety.

EXAMPLE IV

When the procedure of Example I is repeated substituting polyethylenimine 600 (molecular weight 60,000) for polyethylenimine 200 the polymer/dye complex obtained contains approximately 130 dye molecules per molecule of polyethylenimine.

EXAMPLE V

The procedure of Example I is repeated, using under similar conditions, polylysine (mol. wt. 8,000–20,000) in place of polyethylenimine, the isothiocyanate of lissamine Rhodamine-B in place of fluoroscein isothiocyanate, thereby providing a polylysine/rhodamine complex in which each backbone molecule of the complex has a plurality of dye molecules bound thereto. Lissamine Rhodamine B has the structure described in page 379 of *Dyeing and Chemical Technology of Textile Fibres*, Trotman, 45th Ed., C. Griffin & Co., London.

EXAMPLE VI

The substitution of sulfonyl chloride of Lissamine Rhodamine-B in the procedure of Example V also results in the corresponding rhodamine/polymer complex.

EXAMPLE VII

To form a reagent of the present invention (e.g. a dye/polymer antibody complex) Anti-Echo virus antiserum (2.5 Mg.) is dissolved in 0.1 M, pH 7.0 aqueous sodium cacodylate and 1.1 mg. of the polymer/dye complex of Example I is added with stirring. The resultant mixture is stirred for 10 minutes and 1 mg. tris/chloride is added to inhibit cross-linking between antibody molecules. Stirring is continued for 35 more minutes and the mixture is then applied to a Sephadex G-200 column (0.9×60 cm.) (silica gel) equilibrated with 0.1 M, pH 8.5 tris/chloride buffer. The column is eluted with the same buffer and 2 ml. fractions of the reagent are collected.

The optical density of the reagent and of the fractions is determined at 280 nm. and 495 nm. By difference spectral analysis the amount of antibody in each fraction is determined and the amount of dye bound per antibody molecule is estimated. Knowing the number of dye molecules per polymer molecule, the average number of polymer molecules per antibody molecule is calculated. By this assay procedure it was determined that 1.2–1.3 polymer molecules are bound to each antibody molecule.

The immunological activity of the dye/polymer/antibody complex is measured by hemagglutination. By this method it was found that the dye/polymer/antibody complex retained 70% of the activity of the uncombined antibody.

The fluorescence of the dye/polymer/antibody complex is obtained using an Aminco Bowan fluorimeter. Fluorescence is measured in relation to standard solutions of fluoroscein isothiocyanate of concentration 0.001–1.0 ml. Excitation is measured at 495 nm. and emission at 526 nm. Complexes are diluted to give the same optical density at 495 nm. as do the known dilutions of fluoroscein isothiocyanate. The quantum efficiency was determined as 4% for the complex containing polyethylenimine with 80 dye molecules, using for comparison free fluoroscein isothiocyanate as 100%.

The reagent thus prepared is run through a Sephadex column and all fractions discarded except that containing reagent in which a polymer molecule is coupled to only one antibody. When that fraction is mixed with a solution containing Anti-Echo virus as an analyte an antibody-antigen reaction occurs resulting in each viral particle coupling to two or more antibody complexes.

EXAMPLE VIII

To form another reagent of the present invention, the benzaldehyde moiety of the complex of Example III is removed by mild hydrolysis in 1 ml. of 1% HCl in a cooled solution for about three hours, and excess acid removed by dialyzing the solution. Thereafter, water is removed from the solution by evaporation at reduced pressures, and the resulting polymer/dye complex is dissolved in hot acetone. To the acetone solution, 10 equivalents of thiophosgene is added with additional acetone and the mixture refluxed for four hours. The acetone is then evaporated to produce a functionalized polymer/dye complex.

The functionalized polymer/dye complex is dissolved in water, buffered at pH 9.5 with 0.5 m $Na_2CO_3$ and about 2.5 milligrams of Anti-Echo virus antiserum is added. The mixture is stirred continuously for about 16 hours during which time light is excluded from the mixture. Excess dye is then removed by passage through a Sephadex column followed with elution of the column with 0.1 M, pH 7.0 aqueous sodium cacodylate. 2 ml. fractions are collected containing polymer/dye antibody complex in which the polymer-antibody ratio is 1:1.

EXAMPLE IX

Yet another reagent of the present invention useful for detecting the presence of a polyvalent metal, (here specifically nickel) is formed as follows of a ligand for that metal:

To a solution containing 10 mg. of the polymer/dye complex prepared according to Example I is added 0.1 mg. of a ligand, here benzyl p-amino benzyl diisonitrosoethane (i.e. benzyl p-amino glyoxime) and the mixture stirred for one minute. The reaction is terminated then by adding 100 mg. of ethanolamine which has been carbonate buffered to pH 9. The mixture is dialyzed to remove excess ethanolamine and benzyl glyoxime. The resulting reagent when painted onto a dried smear of nickel-containing fluid on a glass slide will coupld approximately four molecules of the polymer/dye/ligand to each nickel atom. The slide is then lightly washed with water to remove excess reagent. On microscopic examination of the slide illuminated with light is the absorption bond of fluoroscein, the presence of nickel atoms will be indicated by the amplitude of fluorescence from each point source which indicates a group of bound complexes.

Certain changes may be made in the above method and produce without departing from the scope of the invention herein involved as will be obvious to one skilled in the art, and it is therefore intended that all matter contained in the above description shall be interpreted in an illustrative and not in a limiting sense.

What is claimed is:

1. A reagent reactive with an analyte body, said reagent comprising;
   a solution containing a plurality of individual molecules of a first reactant, each of said molecules being a chain molecule having a plurality of reactive sites, substantially only one of said sites being specifically reactable with said analyte body in a reaction wherein several of said molecules can become coupled to said analyte body;
   like plurality of polyfunctional polymeric backbone molecules substantially each of which is covalently bonded to only a corresponding one of said molecules of first reactant at another of said sites sterically separated from said one site so as not to impair substantially the specificity of said reaction, each said backbone molecule having coupled thereto radicals or fluorescent dye in a plurality limited so as not to impair substantially the specificity of said reaction.

2. The reagent of claim 1 wherein said first reactant is a protein molecule.

3. The reagent of claim 1 wherein said analyte body is an antigen and said first reactant is an antibody.

4. The reagent of claim 3 wherein said antibody is that which is specific to Hepatitis B antigen.

5. The reagent of claim 1 wherein said analyte body is a polyvalent metal and said first reactant is a ligand.

6. The reagent of claim 5 wherein said ligand is dibenzyl gloxime.

7. The reagent of claim 1 wherein said fluorescent dye is fluorescein.

8. The reagent of claim 1 wherein said dye is Lissamine Rhodamine-B.

9. The reagent of claim 1 wherein said polymeric backbone is a polyethylenimine of molecular weight in the range of 1200–60,000.

10. The reagent of claim 1 wherein said polymeric backbone is a polyethylenimine of molecular weight of substantially 1200.

11. The reagent of claim 1 wherein said polymeric backbone is a polyethylenimine of molecular weight of about 20,000.

12. The reagent of claim 1 wherein said polymeric backbone is a polyethylenimine of molecular weight in the range of 1200 to 60,000 and said fluorescent dye is fluorescein.

13. The reagent of claim 1 wherein the ratio in said reagent molecules of said first reactant to said backbone molecules is substantially 1:1.

14. Method of manufacturing a reagent reactive within an analyte body, said method comprising the steps of
  reacting a polyfunctional polymer molecule with a carbonyl compound to block one or more reactive sites at the ends of the polymeric backbone and thereby provide a protected polymer;
  reacting functionalized molecules of dye with side reactive sites on said polymeric backbone of said protected polymer molecule to thereby provide a dye-tagged polymer molecule; and
  covalently coupling said dye-tagged polymer molecule through one of said end reactive sites to a reactant molecule specifically reactable with said analyte body.

15. Method as defined in claim 14 wherein said carbonyl compound is a monoaldehyde and said step of covalently coupling comprises first removing said monoaldehyde from said one end site by mold hydrolysis so as to reactivate said end site and then reacting the reactivated end site with said reactant molecule.

16. Method as defined in claim 15 wherein said reactant molecule is polyethylenimine.

17. Method as defined in claim 15 wherein said reactant molecule is a polyvalent metal ligand.

18. Method as defined in claim 15 wherein said carbonyl compound is benzaldehyde, said dye is fluorescein isothiocyanate and said polymer is polyethylenimine.

19. Method of detecting analyte bodies in solution, comprising the step of producing a mixture by mixing with said bodies a reagent comprising molecules of reactant each of which has a plurality of reaction sites, substantially one of said sites being specifically reactable with a corresponding one of said analyte bodies, each of said molecules having covalently coupled thereto a single polyfunctional polymeric backbone molecule having in turn coupled thereto a plurality of molecules of fluorescent dye in a number limited so as not to impair substantially the specificity of the reaction between said analyte bodies and said reactant.

20. Method as defined in claim 19 wherein said analyte bodies are antigens and said reactant is antibody.

21. Method as defined in claim 20 wherein said antigens and said antibody are mixed with one another under conditions in which the dye/polymer/antibody in the reagent is substantially electrically neutral.

22. Method as defined in claim 19 including the step of illuminating the mixture of analyte bodies and reactant with radiation in an absorption band of said dye.

23. Method as defined in claim 22 including the additional steps of observing the amplitude of fluorescent emission from each point source thereof when said dye molecules are illuminated and selecting only the emissions having amplitudes above a selected threshold.

24. Method as defined in claim 19 wherein said analyte bodies are polyvalent metal and said reactant is a ligand.

* * * * *